United States Patent
Kimmlingen et al.

(10) Patent No.: US 12,295,712 B2
(45) Date of Patent: May 13, 2025

(54) METHOD FOR MONITORING ABSORPTION, MAGNETIC RESONANCE DEVICE AND COMPUTER PROGRAM PRODUCT

(71) Applicant: Siemens Healthineers AG, Forchheim (DE)

(72) Inventors: Ralph Kimmlingen, Zirndorf (DE); Patrick Liebig, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 327 days.

(21) Appl. No.: 17/878,188

(22) Filed: Aug. 1, 2022

(65) Prior Publication Data
US 2023/0038365 A1 Feb. 9, 2023

(30) Foreign Application Priority Data

Aug. 3, 2021 (DE) ...................... 10 2021 208 408.7

(51) Int. Cl.
*A61B 5/055* (2006.01)
*A61B 5/00* (2006.01)
*G01R 33/28* (2006.01)

(52) U.S. Cl.
CPC ............ *A61B 5/055* (2013.01); *A61B 5/0035* (2013.01); *A61B 5/0037* (2013.01); *A61B 5/7264* (2013.01); *G01R 33/288* (2013.01); *A61B 2576/00* (2013.01)

(58) Field of Classification Search
CPC .... A61B 5/055; A61B 5/0037; G01R 33/288; G01R 33/543
See application file for complete search history.

(56) References Cited

U.S. PATENT DOCUMENTS

| 8,653,818 | B2 | 2/2014 | Adalsteinsson et al. |
| 2011/0043205 | A1 | 2/2011 | Graesslin et al. |
| 2012/0256626 | A1 | 10/2012 | Adalsteinsson et al. |
| 2012/0262174 | A1* | 10/2012 | Voigt ................... G01R 33/443 324/309 |

(Continued)

OTHER PUBLICATIONS

Meliado, E.F. et al: "A deep learning method for image-based subject-specific local SAR assessment"; Magnetic Resonance in Medicine; Year: 2020, vol. 83, pp. 695-711.

*Primary Examiner* — Carolyn A Pehlke
(74) *Attorney, Agent, or Firm* — Harness, Dickey & Pierce, P.L.C.

(57) ABSTRACT

In a method for monitoring absorption of a transmitter output irradiated into a patient by a transmitter unit of a magnetic resonance device, absorption data is provided, which describes a patient-nonspecific, location-dependent absorption sensitivity of the transmitter output to be irradiated. The patient is positioned in an irradiation region of the magnetic resonance device, in which the irradiation of the transmitter output into the patient is to take place. An anatomy of the patient is detected in the irradiation region, and the absorption data is assigned to the anatomy of the patient. A magnetic resonance scan of the patient is then performed, wherein the transmitter output absorbed by the patient is monitored during the magnetic resonance scan based on the absorption data assigned to the anatomy of the patient.

19 Claims, 2 Drawing Sheets

(56) References Cited

U.S. PATENT DOCUMENTS

| | | | |
|---|---|---|---|
| 2013/0271129 A1* | 10/2013 | Kess | G01R 33/3692 |
| | | | 324/322 |
| 2016/0091583 A1 | 3/2016 | Saybasili et al. | |
| 2017/0097396 A1* | 4/2017 | Harvey | A61B 5/0035 |
| 2019/0056465 A1* | 2/2019 | Schnetter | G01R 33/288 |
| 2020/0142057 A1* | 5/2020 | Pendse | G01R 33/5608 |
| 2020/0337592 A1* | 10/2020 | Brada | G01R 33/5608 |

* cited by examiner

METHOD FOR MONITORING ABSORPTION, MAGNETIC RESONANCE DEVICE AND COMPUTER PROGRAM PRODUCT

CROSS-REFERENCE TO RELATED APPLICATION(S)

The present application claims priority under 35 U.S.C. § 119 to German Patent Application No. 10 2021 208 408.7, filed Aug. 3, 2021, the entire contents of which are incorporated herein by reference.

FIELD

One or more example embodiments of the present invention relate to a method for monitoring absorption, a magnetic resonance device and a computer program product.

BACKGROUND

In medical engineering, imaging via magnetic resonance (MR), also called magnetic resonance tomography (MRT) or magnetic resonance imaging (MRI), is characterized by high soft-tissue contrasts. Typically, a human or animal patient is positioned on a patient table in a patient receiving area of a magnetic resonance device. During a magnetic resonance scan a transmitter output in the form of radio-frequency (RF) transmitter pulses is irradiated into the patient, normally with the help of a transmitter unit. The transmitter pulses cause nuclear spins to be excited in the patient, as a result of which magnetic resonance signals are triggered. The magnetic resonance signals are received by the magnetic resonance device and are used for the reconstruction of magnetic resonance images.

Local coils in the form of transmit/receive coils are normally used for signal excitation in magnetic resonance devices using ultra-high magnetic fields, in particular 7 tesla or more, i.e. this type of transmit/receive coil is designed to transmit and receive RF signals. Local coils which are stationary relative to the patient table are generally used in this case. These local coils are generally rigid and/or intended for a particular body region (e.g. head and joints such as the knee, shoulder, hand and foot or torso/abdomen), so as to be able to provide optimum transmission efficiency and field homogeneity.

The transmitter unit of the local coil often comprises multiple transmitter antennas. To homogenize the transmit field, the multiple transmitter antennas can be controlled in a chronologically parallel manner with adjustable phase and amplitude (parallel transmit, pTx). The shapes of the transmitter pulses suitable for this generate a complex sequence of heat inputs into the tissue of the patient. To enable the resulting specific absorption rate (SAR) to be predicted, a precise knowledge of the local field properties is required.

A worst-case approach is conventionally used for the SAR calculations for these coils. SAR simulations are typically performed with different body models and variants (e.g. via morphing and by varying the position) and a sufficient number of RF excitation profiles. In particular, resultant SAR hotspots can be calculated and can be compressed for realtime monitoring during a magnetic resonance scan into matrices containing what are known as virtual observation points (VOPs). An approach such as this is disclosed for example in the printed publication US20120256626A1.

As a result, the SAR monitoring is optimized overall and is safe in respect of the patient population in question, but is unnecessarily limiting for scanning an individual patient. The time needed for the performance of the scan may as a result be significantly increased.

It is true that in research operations individual anatomical test subject measurements, followed by segmentation of the results data, can be performed. This data can then be used for the SAR simulation and calculation of an individual matrix. However, because of the large amount of time it takes and the work involved this procedure is not possible in clinical operation.

SUMMARY

One or more example embodiments of the present invention can in particular be regarded as enabling safe monitoring of the SAR during a magnetic resonance scan in combination with a short scan time.

The object is achieved by the features of the independent claims. Other embodiments are described in the dependent claims.

Thus a method is proposed for monitoring absorption of a (radio-frequency) transmitter output irradiated into a patient by a transmitter unit of a magnetic resonance device. Absorption data is provided, in particular to a system control unit of the magnetic resonance device, which describes a patient-nonspecific, location-dependent absorption sensitivity of the transmitter output to be irradiated. The absorption data preferably takes into account a spatial profile of the transmitter output. The absorption data can for example be present in a memory, in particular a nonvolatile memory, and can be transmitted for provision to the system control unit. The patient is positioned in an irradiation region of the magnetic resonance device, in which the irradiation of the transmitter output into the patient is to take place. For example, the patient is mounted on a patient positioning device and is moved into the isocenter of the magnetic resonance device. Further, an anatomy of the patient is detected in the irradiation region, in particular via a detection unit. The absorption data is assigned to the anatomy of the patient, in particular via the system control unit. Further, a magnetic resonance scan of the patient is performed, wherein the transmitter output absorbed by the patient is monitored during the magnetic resonance scan on the basis of the absorption data assigned to the anatomy of the patient, in particular via the system control unit. During the magnetic resonance scan magnetic resonance signals are normally detected, from which one or more magnetic resonance images can be reconstructed.

In this case the transmitter output irradiated into the patient during the magnetic resonance scan is preferably monitored on the basis of the absorption data assigned to the anatomy of the patient.

The absorption by the patient of the transmitter output irradiated into the patient by the transmitter unit of the magnetic resonance device corresponds in particular to the specific absorption rate, i.e. the monitoring entails SAR monitoring. The monitoring of the transmitter output absorbed by the patient during the magnetic resonance scan on the basis of the assigned absorption data therefore preferably comprises SAR monitoring. By assigning the (patient-nonspecific) absorption data to the (patient-specific) anatomy of the patient the monitoring can preferably be individually adjusted more closely to the patient, without absorption data having to be determined completely afresh for this. Instead, use can be made of general absorption data, which however is adjusted individually. As a result, unnecessary safety margins can advantageously be reduced and the time taken for the performance of the magnetic resonance scan of the patient can be reduced.

The monitoring of the transmitter output absorbed by the patient can in particular comprise monitoring of a shape and/or amplitude and/or rate of RF transmitter pulses emitted by the transmitter unit. The transmitter unit can for this purpose comprise at least one transmitter antenna. In particular, by applying an electrical voltage to the at least one transmitter antenna an RF transmitter pulse can be generated. The monitoring can in particular be performed in realtime during the magnetic resonance scan, i.e. the evaluation of the data needed for the monitoring takes place virtually instantaneously or takes only a short period of time. If appropriate the magnetic resonance scan can be aborted if the transmitter output absorbed by the patient exceeds a predefined limit value.

The absorption data preferably takes account of a free variation of a transmit profile of the transmitter unit in amplitude and/or phase. The transmitter unit preferably comprises multiple transmitter antennas. For example, the transmitter unit is designed as an N-channel array transmit coil. Each transmitter antenna is preferably designed to transmit a transmitter pulse independently of the other transmitter antennas. The multiple transmitter antennas are advantageously free to determine the transmit profile in amplitude and/or phase. In particular, the transmitter unit is designed to transmit a pTx pulse.

The SAR normally depends in particular on the anatomy of the patient, in particular on the load represented by the patient. In the case of a 1-channel transmit coil the SAR can preferably be described by a scalar. In the case of an N-channel array transmit coil the SAR can in particular be described by a vector.

When transmitter output is irradiated into the patient via a transmitter unit with multiple transmitter antennas it is particularly advantageous to determine at least one SAR matrix on the basis of the assigned absorption data. The at least one SAR matrix can in particular contain virtual observation points. Previously calculated SAR hotspots are advantageously compressed in the virtual observation points.

The absorption data is in particular not specific to the patient on whom the said magnetic resonance scan is being performed. In particular, the absorption data can be data which takes into account a plurality of patient types and/or a group of patient types and/or a patient population. In particular, the absorption data can map a worst case, in particular a worst-case scenario; for example, a most unfavorable case can be assumed during the generation of the absorption data. It can advantageously be ensured on the basis of the absorption data that regardless of the patient's individual configuration no risk to the patient is posed by the absorption of the irradiated transmitter output.

The absorption data is preferably generated beforehand, in other words in particular before the patient is positioned, for example by simulation and/or on the basis of previously generated scan data. To generate this scan data magnetic resonance scans can for example be performed on a plurality of patients.

The absorption sensitivity can in particular be an assumed sensitivity of the absorption of the transmitter output to be irradiated in the body of the patient. In particular, fixed points can exist in the irradiation region, at which the transmitter output to be irradiated is absorbed more strongly, as well as other fixed points, at which it is absorbed more weakly.

The transmitter unit can in particular be part of a local coil. The irradiation region can in particular be determined by the local coil. For example, the irradiation region is situated in a space which is at least partially surrounded by the local coil. For example, the local coil is a head coil with an upper part and a lower part and in an operational state of the local coil the irradiation region is situated between the upper part and the lower part. The local coil can for example also be a knee coil and/or a foot coil, which enclose the irradiation region at least partially. The local coil can however for example be a spine coil and/or a coil cover, which do not enclose the irradiation region. The positioning of the patient in the irradiation region of the magnetic resonance device can for example comprise mounting the patient's head in a head coil.

The detected anatomy of the patient can for example comprise a spatial contour and/or shape and/or elongation and/or extent of at least one part of the patient's body.

The assignment of the absorption data to the anatomy of the patient can in particular comprise an assignment of a value of the absorption sensitivity of the transmitter output to be irradiated to a point and/or region in the irradiation region. In particular, at least one SAR matrix can be created by taking account of the assigned absorption data. The SAR matrix can in particular for each voxel contain an SAR (e.g. a 10 g local SAR) relating to a determined mass of a local volume, which in particular can be formed for all relevant linear combinations of a transmit vector (e.g. for an N channel transmit system N×N linear combinations).

The performance of the magnetic resonance scan on the patient can in particular comprise irradiating an imaging magnetic resonance sequence and/or receiving imaging magnetic resonance signals.

The monitoring of the irradiated transmitter output can in particular comprise a comparison of the transmitter output absorbed by the patient with a predetermined comparison value, in particular a limit value. If this is exceeded, the magnetic resonance scan can for example be aborted and/or a warning given, in particular to an operator of the magnetic resonance device.

A further form of embodiment of the method provides that during the magnetic resonance scan the transmitter output is irradiated via multiple transmitter antennas of the transmitter unit, wherein the absorption data takes account in amplitude and/or phase of a transmit profile generated by the multiple transmitter antennas. In particular, the transmit profile can also be generated by a linear combination of the respective amplitudes and/or phases of the multiple transmitter antennas, for example N amplitudes and N phases of N transmitter antennas.

A further form of embodiment of the method provides that the absorption data comprises virtual observation points (VOP) for monitoring the transmitter output absorbed by the patient, wherein each observation point represents at least one voxel, in particular a voxel cluster.

Preferably a peak sensitivity for a local specific absorption rate is assigned to the at least one voxel. Preferably each voxel cluster defines a virtual observation point with a peak sensitivity compared to a local specific absorption rate for the voxel cluster. Preferably generation of virtual observation points comprises compression of a patient model into a plurality of voxel clusters. In particular, voxels can be collected together in a model and assigned to a cluster of voxels which are represented by one of the virtual observation points. Further possible aspects and advantages for the concept of monitoring the absorption of the transmitter output irradiated into the patient via virtual observation points can be taken from the printed publication U.S. Pat. No. 8,653,818 B2.

A further form of embodiment of the method provides that the assignment of the absorption data to the anatomy of the patient takes place via a neural network, in particular a previously trained neural network. For example, a neural network such as this is based on pattern recognition. As a result, the assignment can advantageously take place particularly precisely and/or reliably.

A further form of embodiment of the method provides that the position data describes a position of the transmitter unit of the magnetic resonance device prior to and/or during the performance of the magnetic resonance scan. For example, the position data describes a position of a local coil which comprises the transmitter unit.

A further form of embodiment of the method provides that the method further comprises a detection of position data, wherein the position data describes a position of the patient in the irradiation region relative to the transmitter unit of the magnetic resonance device prior to and/or during the performance of the magnetic resonance scan.

The assignment of the absorption data to the anatomy of the patient can advantageously take place particularly precisely and/or reliably with the help of the detected position data. In particular, the monitoring of the absorption of the transmitter output irradiated into the patient by the transmitter unit of the magnetic resonance device can take into account any changes in position during the magnetic resonance scan on the basis of the detected position data.

The magnetic resonance device preferably comprises a separate sensor unit to detect the position data. This sensor unit preferably detects the position of the transmitter unit and/or the position of the patient in the irradiation region relative to the transmitter unit independently of a receiving unit of the magnetic resonance device for receiving magnetic resonance signals.

Advantageously with the help of the separate sensor unit the assignment of the absorption data to the anatomy of the patient can take place particularly quickly and/or safely. Any changes in the position of the patient are advantageously taken into account immediately or with only a slight (time) delay, so that a particularly high level of patient safety can be achieved. In particular, when the position data is detected via a separate sensor unit it is possible to dispense with a time-consuming measurement and/or evaluation of any magnetic resonance signals to determine the position.

The detection of the position data advantageously preferably does not include the detection of magnetic resonance signals. The detection of the position data preferably includes the detection of optical signals. For example, the sensor unit comprises a camera, in particular a 3D camera, for this purpose.

Advantageously with the help of the detected position data the assignment of the absorption data to the anatomy of the patient can take place particularly quickly and/or safely.

A further form of embodiment of the method provides that the method further comprises a synchronization of position data, in particular the detected position of the patient in the irradiation region relative to the transmitter unit of the magnetic resonance device, with patient registration data and/or magnetic resonance device data.

The position data can in particular be used to identify a discrepancy (intended or unintended) with the patient registration data. This type of discrepancy may possibly result in an excessive SAR dose. This risk can advantageously be reduced by synchronizing two independent instances.

The magnetic resonance device data can for example include information as to whether a local coil, which in particular includes the transmitter unit, is connected to the magnetic resonance device.

A further form of embodiment of the method provides that detection of the anatomy of the patient in the irradiation region includes detection of magnetic resonance signals by the magnetic resonance device. The detection of the anatomy of the patient in the irradiation region can preferably take place by detection of a scout image prior to the performance of the (actual) magnetic resonance scan, during which the transmitter output absorbed by the patient is monitored on the basis of the assigned absorption data.

A further form of embodiment of the method provides that the detection of the anatomy of the patient in the irradiation region takes place in a monitoring mode that takes into account a worst case of an absorption of the irradiated transmitter output by the patient. In particular, this monitoring mode does not provide any patient-specific monitoring at all, or at any rate no patient-specific monitoring on the basis of absorption data assigned to the anatomy of the patient. Thus this type of monitoring mode differs from the intended monitoring during the (actual) magnetic resonance scan.

Further, a magnetic resonance device is proposed which is designed to execute a method described above for monitoring absorption of a transmitter output irradiated into a patient by a transmitter unit of a magnetic resonance device.

The advantages of the inventive magnetic resonance device substantially correspond to the advantages of the inventive method for monitoring absorption of a transmitter output irradiated into a patient by a transmitter unit of a magnetic resonance device, which are explained in detail above. Features, advantages or alternative forms of embodiment can here likewise be transferred to the other claimed subject matters and vice versa.

A computer program product is further proposed, which comprises a program that can be loaded directly into a memory of a programmable system control unit of a magnetic resonance device and that contains program instructions, code or means, e.g. libraries and auxiliary functions, for executing an inventive method for monitoring absorption of a transmitter output irradiated into a patient by a transmitter unit of a magnetic resonance device, when the computer program product is executed in the system control unit of the magnetic resonance device.

The computer program product can in this case comprise software with a source code which still has to be compiled and linked or which only has to be interpreted, or an executable software code which only has to be loaded into the system control unit for execution. Thanks to the computer program product the inventive method can be executed quickly, identically reproducibly and robustly. The computer program product is configured such that via the system control unit it can execute the inventive method steps. The system control unit must in each case meet the requirements, for example a corresponding main memory, a corresponding graphics card or a corresponding logic unit, such that the respective method steps can be executed efficiently.

The computer program product is for example stored on a computer-readable medium or is archived on a network or server, from where it can be loaded into the processor of a local system control unit, it being possible for said processor to be directly connected to the magnetic resonance device or to be designed as part of the magnetic resonance device.

Furthermore, control information of the computer program product can be stored on an electronically readable data storage medium.

The control information of the electronically readable data storage medium can be configured such that when the data storage medium is used in a system control unit of a magnetic resonance device it performs an inventive method. Examples of electronically readable data storage media are a DVD, a magnetic tape or a USB stick, on which electronically readable control information, in particular software, is stored. When this control information is read from the data storage medium and stored in a system control unit of the magnetic resonance device, all inventive forms of embodiment of the previously described method can be performed. Thus example embodiments of the present invention can also be based on the said computer-readable medium and/or the said electronically readable data storage medium.

BRIEF DESCRIPTION OF THE DRAWINGS

Further advantages, features and details of the present invention emerge from the exemplary embodiments described below and on the basis of the drawings. Parts corresponding to one another are provided with the identical reference characters in all figures, in which.

DETAILED DESCRIPTION

Figure 1:
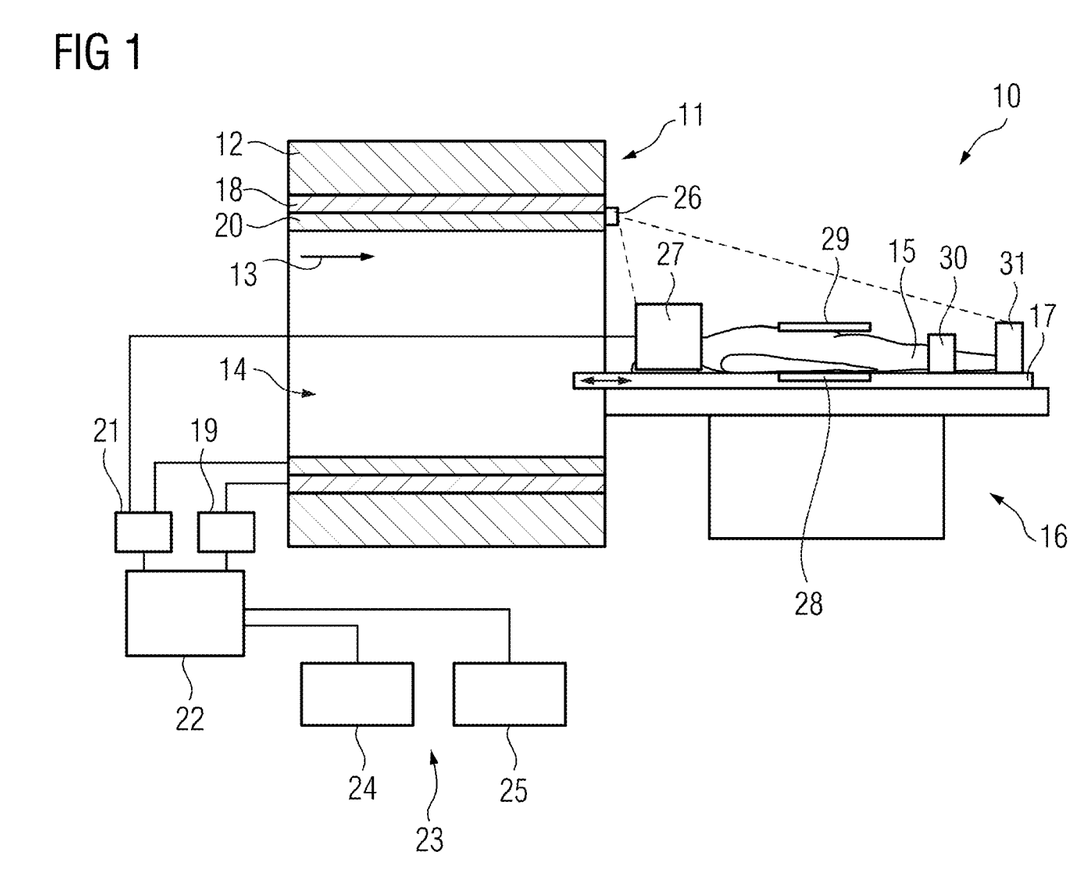
FIG. 1 shows a magnetic resonance device in a schematic representation, according to one or more example embodiments of the present invention.

FIG. 1 schematically represents a magnetic resonance device 10. The magnetic resonance device 10 comprises a magnet unit 11, which contains a main magnet 12 for generating a strong main magnetic field 13, which is in particular constant over time. Moreover, the magnetic resonance device 10 comprises a patient receiving area 14 to receive a patient 15. The patient receiving area 14 in the present exemplary embodiment is designed as cylindrical and is cylindrically surrounded in a circumferential direction by the magnet unit 11. An embodiment of the patient receiving area 14 which differs from this is however in principle always conceivable. The patient 15 can be moved into the patient receiving area 14 via a patient positioning device 16 of the magnetic resonance device 10. The patient positioning device 16 has for this purpose a patient table 17 configured to be movable inside the patient receiving area 14.

The magnet unit 11 further has a gradient coil unit 18 to generate magnetic field gradients that are used for position encoding during imaging. The gradient coil unit 18 is controlled via a gradient control unit 19 of the magnetic resonance device 10. The magnet unit 11 further comprises a radio-frequency antenna unit 20, which in the present exemplary embodiment is designed as a body coil permanently integrated into the magnetic resonance device 10. The radio-frequency antenna unit 20 is controlled by a radio-frequency antenna control unit 21 of the magnetic resonance device 10 and with the help of its transmitter unit irradiates radio-frequency magnetic resonance sequences into an irradiation region, which here is situated in the patient receiving area 14 of the magnetic resonance device 10. As a result, a transmitter output is irradiated into the irradiation region and is at least partially absorbed by the patient 15. As a result an excitation of atomic nuclei occurs in the main magnetic field 13 generated by the main magnet 12. Magnetic resonance signals are generated by relaxation of the excited atomic nuclei. The radio-frequency antenna unit 20 is designed to receive the magnetic resonance signals.

Furthermore, the magnetic resonance device can comprise one or more local coils, which are arranged close to the patient 15. By way of example, a head coil 27, a spine coil 28, a coil cover 29, a knee coil and a foot coil 31 are represented here. (Mostly however not so many local coils are used at the same time.) The local coils are controlled by the radio-frequency antenna control unit 21, wherein for reasons of clarity only the head coil 27 is represented here as connected to the radio-frequency antenna control unit 21. Often local coils comprise only one receiving unit for receiving magnetic resonance signals. However, the local coils represented here also comprise a transmitter unit, by which a transmitter output can be irradiated into the patient 15. Particularly in the case of magnetic resonance devices with a high main magnetic field 13 of, for example, more than 5 tesla, the irradiation of the magnetic resonance sequences is performed not by a body coil permanently incorporated into the magnetic resonance device, but by local coils with a transmitter unit; moreover, such local coils mostly comprise a receiving unit for receiving magnetic resonance signals.

The magnetic resonance device 10 has a system control unit 22 to control the main magnet 12, the gradient control unit 19 and the radio-frequency antenna control unit 21. The system control unit 22 controls the magnetic resonance device 10 centrally, such as for example the performance of a predetermined imaging gradient echo sequence. Further, a computer program can be executed in the system control unit to monitor absorption of a transmitter output irradiated into a patient 15 by a transmitter unit of the magnetic resonance device 10. Moreover, the system control unit 22 comprises an evaluation unit, not shown in greater detail, to evaluate the magnetic resonance signals that are detected during the magnetic resonance examination. Furthermore, the magnetic resonance device 10 comprises a user interface 23 that is connected to the system control unit 22. Control information such as for example imaging parameters, as well as reconstructed magnetic resonance images, can be displayed for a medical operative on a display unit 24, for example on at least one monitor, of the user interface 23. Furthermore, the user interface 23 has an input unit 25, via which information and/or parameters can be input by the medical operative during a scanning procedure.

Further, the magnetic resonance device 10 includes a sensor unit in the form of a camera 26, in particular a 3D camera, with which the position of the local coils 27, 28, 29, 30, 31 with their transmitter units and/or of the patient 15 can be detected. The camera 26 can detect the position data in the form of optical signals. The camera 26 has a detection range (indicated by the dashed lines) which is suitable for detecting the position of the local coils 27, 28, 29, 30, 31 and thus also the transmitter units arranged in the local coils 27, 28, 29, 30, 31. (Data is advantageously provided to the system control unit 22 to enable the position of the transmitter units arranged in the local coils 27, 28, 29, 30, 31 to be derived from the position of the local coils 27, 28, 29, 30, 31. This data can for example include information about the structure, in particular the geometric structure, of the local coils 27, 28, 29, 30, 31.) This position data is therefore detected independently of the detection of the magnetic resonance signals, which can be detected with the help of receiving units of the body coil and/or of the local coils 27, 28, 29, 30, 31. The position data detected by the camera 26 is transmitted to the system control unit 22 for further evaluation.

Figure 2:
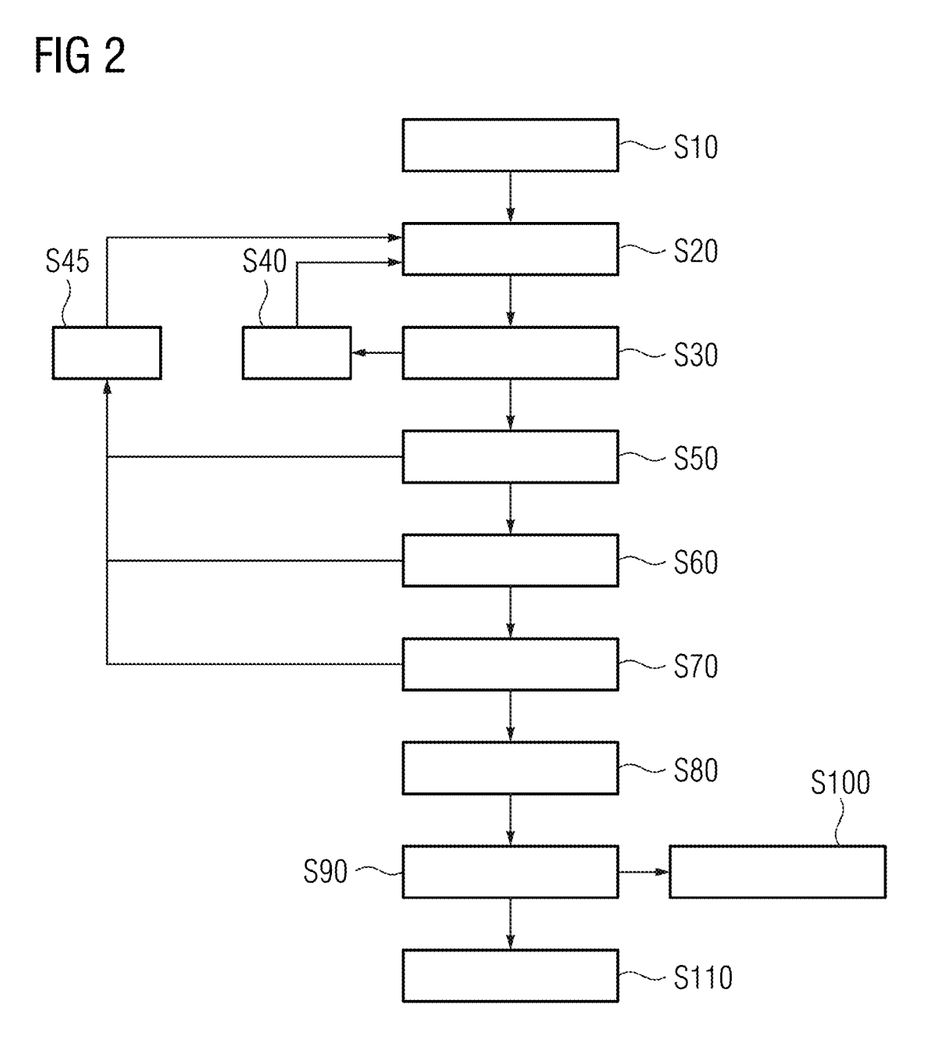
FIG. 2 shows a method for monitoring absorption according to one or more example embodiments of the present invention.

FIG. 2 shows by way of example a method for monitoring absorption of a transmitter output irradiated into a patient 15 by a transmitter unit of a magnetic resonance device 10.

In S10 the patient 15 is positioned in an irradiation region of the magnetic resonance device 10, in which the irradiation of the transmitter output into the patient 15 is to take place. Depending on the transmitter unit used the irradiation region can be embodied differently. For example, if the transmitter unit of the body coil permanently incorporated into the magnetic resonance device 10 is used, this normally results in a comparatively large irradiation region in the patient receiving area 14. For example, if a local coil 27, 28, 29, 30, 31 is the active coil and if its transmitter unit is used, this normally results in a comparatively small, locally concentrated irradiation region. For example, when the knee coil 30 is used the irradiation region is normally situated only inside the small region on the knee of the patient 15, which is surrounded by the knee coil 30.

In S20 position data is detected, wherein the position data describes a position of the transmitter unit of the magnetic resonance device 10 prior to and/or during the performance of the magnetic resonance scan. This can be done for example with the help of the camera 26. As a result, the position of the active transmit coil, for example the knee coil 30, can be determined.

In S30 the detected position data, in particular the determined position of the active coil, is synchronized with patient registration data and/or magnetic resonance device data. Patient registration data is for example patient-specific data, such as e.g. age, sex, weight and/or height of the patient 15, which was input prior to the magnetic resonance examination into a data detection system connected to the magnetic resonance device 10. Magnetic resonance device data is for example data that describes the status and/or properties of the magnetic resonance device 10. Synchronizing the data enables the consistency of the position data, the patient registration data and/or the magnetic resonance device data to be checked. For example, the consistency check can reveal that the active coil is not connected to or plugged into the magnetic resonance device 10.

If an error and/or an inconsistency is found during the synchronization, a correction measure can be taken in S40, which can for example take the form of an interaction by the operative of the magnetic resonance device 10. Thus for example a coil that is initially not connected can be correctly connected to the magnetic resonance device, at which point the position data is again detected in S20.

If the consistency check in S30 is successful, an anatomy of the patient 15 in the irradiation region can be detected in S50. For this, overview data can for example be measured. The detection of the anatomy of the patient 15 can take place by magnetic resonance signals being detected by the magnetic resonance device 10. In particular, at least one magnetic resonance image can be generated on the basis of detected magnetic resonance signals, on the basis of which the anatomy of the patient 15 can be determined. To guarantee a high level of safety for the patient 15, the detection of the anatomy of the patient can take place in a monitoring mode, which takes into account a worst case of an absorption of the irradiated transmitter output by the patient. This type of monitoring mode can in particular be what is known as a "protected mode", which includes the worst case for all body regions and models.

To be sure, taking account of the worst case can mean that the performance of the magnetic resonance device 10 is reduced; however, ideally the detection of the anatomy of the patient 15 takes place just once, so that this does not result in any significant restriction of the overall magnetic resonance examination of the patient 15.

In S60 absorption data is provided to the system control unit 22, and describes a patient-nonspecific, location-dependent absorption sensitivity of the transmitter output to be irradiated. The absorption data can for example include virtual observation points. In this case each observation point can in particular represent a voxel cluster. A peak sensitivity for a local specific absorption rate can be assigned to the voxel cluster.

In S70 the absorption data is assigned to the anatomy of the patient 15 by the system control unit 22. This assignment can in particular take place via a neural network.

If an error occurs in S50, S60 or S70, a correction measure can also be taken in S45, for example in the form of an interaction by the operative of the magnetic resonance device 10.

In S80 the assigned absorption data is accepted, possibly following confirmation by the operative. In S90 a magnetic resonance scan of the patient 15 is performed, wherein during the magnetic resonance scan the transmitter output absorbed by the patient 15 is monitored on the basis of the assigned absorption data.

During the magnetic resonance scan, position data is detected in S90. In particular, in this case the position of the active transmit coil, in other words e.g. the knee coil 30, is determined. On the basis of the position data the patient 15 can be monitored during the magnetic resonance scan, so that if the patient moves too much and/or if the coil is displaced the scan can be aborted. If for example the deviation in the actual position of the active transmit coil from the target position exceeds a predetermined limit value, the magnetic resonance scan is aborted in S100. As a result, patient safety can advantageously be increased. Otherwise the magnetic resonance scan terminates in S110 according to plan.

The determination of the position of the active transmit coil in S20 and S90 together with the evaluation based thereon of the position data can be understood as a first safety shell of the magnetic resonance examination of the patient 15. The measurement of the overview data in S50 with the active transmit coil, the assignment in S70 of the absorption data provided in S60 together with the SAR monitoring based thereon in S90 can be understood as a second safety shell of the magnetic resonance examination of the patient 15. These safety shells are advantageously independent of one another, so that patient safety can be guaranteed in clinical operation.

By individualizing the SAR monitoring as a function of the anatomy of the body of the patient 15, worst-case additions can be prevented, so that for example more scanning layers can be recorded and/or the scan time can be reduced. The proposed method can advantageously also easily be retrofitted into existing MR systems, for example by implementation of suitable software and/or hardware, such as e.g. a 3D camera.

In conclusion it is once again pointed out that the methods described in detail above and the magnetic resonance device represented are merely exemplary embodiments that can be modified in a wide variety of ways by the person skilled in the art, without departing from the scope of the present invention. Furthermore, the use of the indefinite article "a" or "an" does not rule out that the features in question may also be present multiple times. Likewise, the term "unit" does not rule out that the components in question consist of multiple interacting subcomponents, which where appropriate may also be spatially distributed.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been illustrated and described in more detail on the basis of example embodiments embodiment, the present invention is not limited by the disclosed examples and other variations can be derived herefrom by the person skilled in the art without leaving the scope of protection of the present invention.

What is claimed is:

1. A method for monitoring absorption of a transmitter output irradiated into a patient by a transmitter of a magnetic resonance device, the method comprising:
   provisioning absorption data describing a patient-nonspecific, location-dependent absorption sensitivity of the transmitter output to be irradiated;
   positioning the patient in an irradiation region of the magnetic resonance device, the irradiation region being a region in which irradiation of the transmitter output into the patient is to take place;
   detecting an anatomy of the patient in the irradiation region;
   assigning the absorption data to the anatomy of the patient;
   performing a magnetic resonance scan of the patient;
   detecting first position data, the first position data describing a position of the transmitter of the magnetic resonance device at least one of prior to or during the magnetic resonance scan;
   monitoring, during the magnetic resonance scan, the transmitter output absorbed by the patient based on the absorption data assigned to the anatomy of the patient; and
   stopping the magnetic resonance scan in response to the first position data indicating the position of the transmitter is more than a threshold amount different from a target position.

2. The method as claimed in claim 1, further comprising:
   irradiating, during the magnetic resonance scan, the transmitter output via multiple transmitter antennas of the transmitter, wherein
      the absorption data takes into account a transmit profile generated by the multiple transmitter antennas.

3. The method as claimed in claim 2, wherein the transmit profile includes at least one of an amplitude or a phase.

4. The method as claimed in claim 2, wherein the assigning assigns the absorption data to the anatomy of the patient via a neural network.

5. The method as claimed in claim 1, wherein the absorption data contains virtual observation points for monitoring the transmitter output absorbed by the patient, wherein each virtual observation point represents at least one voxel.

6. The method as claimed in claim 5, further comprising: assigning, to the at least one voxel, a peak sensitivity for a local specific absorption rate.

7. The method as claimed in claim 5, wherein each virtual observation point represents a voxel cluster.

8. The method as claimed in claim 1, wherein the assigning assigns the absorption data to the anatomy of the patient via a neural network.

9. The method as claimed in claim 1, further comprising: detecting second position data, the second position data describing a position of the patient in the irradiation region relative to the transmitter of the magnetic resonance device at least one of prior to or during the magnetic resonance scan.

10. The method as claimed in claim 9, further comprising:
    determining, based on the second position data, movement of at least one of the patient or the transmitter; and
    aborting the magnetic resonance scan in response to determining that the movement exceeds a threshold limit value.

11. The method as claimed in claim 1, wherein the detecting of the first position data comprises:
    detecting optical signals via a camera.

12. The method as claimed in claim 1, further comprising:
    determining, based on the first position data, movement of at least one of the patient or the transmitter; and
    aborting the magnetic resonance scan in response to determining that the movement exceeds a threshold limit value.

13. The method as claimed in claim 1, further comprising:
    comparing the first position data with at least one of patient registration or magnetic resonance device data.

14. The method as claimed in claim 13, wherein the magnetic resonance device data includes information indicating whether a local coil is connected to the magnetic resonance device.

15. The method of claim 14, wherein the local coil includes the transmitter.

16. The method as claimed in claim 1, wherein the detecting of the anatomy of the patient in the irradiation region includes detecting magnetic resonance signals by the magnetic resonance device.

17. The method as claimed in claim 1, wherein
    the detecting of the anatomy of the patient in the irradiation region takes place in a monitoring mode, and
    the monitoring mode takes into account a worst case of absorption of the transmitter output by the patient.

18. A non-transitory computer readable medium storing a computer program that, when executed by at least one processor of a magnetic resonance device, causes the magnetic resonance device to perform the method of claim 1.

19. A magnetic resonance device, comprising:
    processing circuitry configured to cause the magnetic resonance device to
       provision absorption data describing a patient-nonspecific, location-dependent absorption sensitivity of a transmitter output to be irradiated,
       position the patient in an irradiation region of the magnetic resonance device, the irradiation region being a region in which irradiation of the transmitter output into the patient is to take place, detect an anatomy of the patient in the irradiation region,
assign the absorption data to the anatomy of the patient,
perform a magnetic resonance scan of the patient,
detect first position data, the first position data describing a position of the transmitter of the magnetic resonance device at least one of prior to or during the magnetic resonance scan,
monitor, during the magnetic resonance scan, the transmitter output absorbed by the patient based on the absorption data assigned to the anatomy of the patient, and
stop the magnetic resonance scan in response to the first position data indicating the position of the transmitter is more than a threshold amount different from a target position.

\* \* \* \* \*